US010987001B2

(12) United States Patent
Carr (10) Patent No.: US 10,987,001 B2
(45) Date of Patent: Apr. 27, 2021

(54) HEATING/SENSING CATHETER APPARATUS FOR MINIMALLY INVASIVE APPLICATIONS

(71) Applicant: Applied ThermoLogic, LLC, Woolwich, ME (US)

(72) Inventor: Kenneth L. Carr, Woolwich, ME (US)

( * ) Notice: Subject to any disclaimer, the term of this patent is extended or adjusted under 35 U.S.C. 154(b) by 0 days.

(21) Appl. No.: 15/721,008

(22) Filed: Sep. 29, 2017

(65) Prior Publication Data

US 2018/0020925 A1    Jan. 25, 2018

Related U.S. Application Data

(63) Continuation of application No. 14/017,812, filed on Sep. 4, 2013, now abandoned, which is a continuation
(Continued)

(51) Int. Cl.
*A61B 5/01* (2006.01)
*A61N 5/02* (2006.01)
(Continued)

(52) U.S. Cl.
CPC .............. *A61B 5/01* (2013.01); *A61B 18/18* (2013.01); *A61B 18/1815* (2013.01); *A61N 5/025* (2013.01); *A61N 5/045* (2013.01); *A61B 2018/00011* (2013.01); *A61B 2018/00029* (2013.01); *A61B 2018/00577* (2013.01);
(Continued)

(58) Field of Classification Search
CPC .......... A61B 2018/00011; A61B 2018/00029; A61N 1/403; H04J 1/00; H04J 14/00; H04B 1/0057; H04B 10/2503
See application file for complete search history.

(56) References Cited

U.S. PATENT DOCUMENTS 2,461,834 A   2/1949 Morin
3,461,499 A   8/1969 Nevin et al.
(Continued)

OTHER PUBLICATIONS

Back to Basics: Impedance Matching (Part 1) by Lou Frenzel; pub. online by Electronic Design on Oct. 24, 2011, accessed Aug. 27, 2015.*
(Continued)

*Primary Examiner* — Katherine L Fernandez
*Assistant Examiner* — Michael S Kellogg (57) ABSTRACT

Catheter apparatus comprises a coaxial cable having proximal and distal ends. The cable includes a hollow center conductor, an outer conductor and an electrically insulating layer between the conductors. An antenna is at the distal end of the cable, and a diplexer is connected to the cable, the diplexer including a transmit path for connecting the antenna to a transmitter which transmits first frequency signals and a receive path for connecting the antenna to a receiver which detects second frequency signals the diplexer isolating the signals on the two paths from one another. A transmission line connects the cable to the diplexer, the transmission line having a segment with a tubular inner conductor one end of which is connected to the center conductor and a second end of which is adapted for connection to a coolant source, the center and inner conductors forming a continuous coolant pathway.

42 Claims, 5 Drawing Sheets

Related U.S. Application Data of application No. 13/709,434, filed on Dec. 10, 2012, now abandoned.

(60) Provisional application No. 61/635,348, filed on Apr. 19, 2012.

(51) Int. Cl.
*A61B 18/18* (2006.01)
*A61N 5/04* (2006.01)
*A61N 1/40* (2006.01)
*A61B 18/00* (2006.01)

(52) U.S. Cl.
CPC ............ *A61B 2018/00791* (2013.01); *A61B 2018/1861* (2013.01); *A61N 1/403* (2013.01)

(56) References Cited

U.S. PATENT DOCUMENTS

| | | | |
|---|---|---|---|
| 3,685,147 A | 8/1972 | Nevin et al. | |
| 3,864,509 A | 2/1975 | Gommans | |
| 4,181,486 A | 1/1980 | Saito | |
| 4,378,267 A | 3/1983 | Saito | |
| 4,910,998 A | 3/1990 | Willis et al. | |
| 5,364,336 A | 11/1994 | Carr | |
| 5,683,382 A * | 11/1997 | Lenihan | A61B 18/18 606/33 |
| 5,742,002 A | 4/1998 | Arredondo et al. | |
| 6,424,869 B1 * | 7/2002 | Carr | A61B 18/18 607/101 |
| 6,878,147 B2 * | 4/2005 | Prakash | A61B 18/18 606/33 |
| 7,197,356 B2 | 3/2007 | Carr | |
| 7,769,469 B2 | 8/2010 | Carr et al. | |
| 2001/0016762 A1 * | 8/2001 | Carr | A61B 18/18 607/101 |
| 2002/0019627 A1 * | 2/2002 | Maguire | A61B 18/1492 606/27 |
| 2002/0079128 A1 * | 6/2002 | Karrmann | H01B 7/0233 174/113 AS |
| 2004/0133254 A1 | 7/2004 | Sterzer et al. | |
| 2004/0243004 A1 * | 12/2004 | Carr | A61B 5/01 600/467 |
| 2007/0219548 A1 * | 9/2007 | Carr | A61B 18/18 606/33 |
| 2007/0299488 A1 * | 12/2007 | Carr | A61B 5/01 607/101 |
| 2008/0033424 A1 * | 2/2008 | van der Weide | A61B 18/18 606/41 |
| 2009/0299360 A1 * | 12/2009 | Ormsby | A61B 8/0841 606/33 |
| 2010/0076424 A1 * | 3/2010 | Carr | A61B 5/01 606/33 |
| 2010/0185191 A1 * | 7/2010 | Carr | A61B 5/0507 606/33 |
| 2013/0281851 A1 | 10/2013 | Carr | |
| 2014/0012132 A1 | 1/2014 | Carr et al. | |
| 2014/0018697 A1 | 1/2014 | Allison | |

OTHER PUBLICATIONS

Back to Basics: Impedance Matching (Part 1) by Lou Frenzel, pub. online by Electronic Design on Oct. 24, 2011, accessed on Aug. 27, 2015.

International Search Report with Written Opinion corresponding to International Application No. PCT/US2013/035558, dated Dec. 16, 2013.

* cited by examiner

HEATING/SENSING CATHETER APPARATUS FOR MINIMALLY INVASIVE APPLICATIONS

CROSS-REFERENCE TO RELATED APPLICATIONS

The present application claims priority from U.S. Provisional Patent Application No. 61/635,348 filed Apr. 19, 2012 by Kenneth L. Carr for an INTEGRATED MICROWAVE CATHETER AND CABLE and is a continuation of copending U.S. patent application Ser. No. 14/017,812, which was filed on Sep. 4, 2013, by Kenneth L. Carr for a HEATING/SENSING CATHETER APPARATUS FOR MINIMALLY INVASIVE APPLICATIONS, which is a continuation of copending U.S. patent application Ser. No. 13/709,434, which was filed on Dec. 10, 2012, by Kenneth L. Carr for a HEATING/SENSING CATHETER APPARATUS FOR MINIMALLY INVASIVE APPLICATIONS, all of which are hereby incorporated by reference.

BACKGROUND OF THE INVENTION

1. Field of the Invention

This invention relates to medical catheter apparatus for minimally invasive applications. It relates especially to catheter apparatus which utilizes electromagnetic radiation to simultaneously controllably heat, and detect the temperature of, fluid or tissue in a human or animal body. The apparatus includes an antenna catheter which is essentially a long flexible cable having a distal end or probe containing an antenna. In order to perform its function, the catheter must be small in diameter and flexible so that it can be threaded along blood vessels and other natural passages in the body to position the antenna at a selected target site.

By placing the catheter probe at the region of interest in the body, one may warm blood and/or ablate tissue to treat tumors, cardiac arrhythmias, renal disease, benign prosthetic hyperplasia (BPH) and the like.

The proximal end of the catheter cable may be connected to an external control unit which includes a transmitter for transmitting electromagnetic energy via the cable to the antenna in the catheter tip in order to heat fluid or tissue, and a receiver which detects thermal emissions picked up by the antenna reflecting the temperature of that fluid or tissue. The receiver outputs a corresponding temperature signal to control a display which displays that temperature. The same signal may also be used to control the transmitter to maintain a selected heating profile.

For apparatus detecting thermal emissions in the microwave range which is of primary interest here, the receiver is usually a radiometer. Every component of a radiometer generates noise power that contributes to the overall noise of the system. Therefore, the total radiometer output signal contains not only noise received by the antenna, but also noise generated within the apparatus itself. Such variations within the apparatus can produce output signal fluctuations that are sometimes greater than the useful signal level to be measured. To overcome these gain variations, Dicke developed the common load comparison radiometer which utilizes a switch, aka a Dicke switch, to alternately connect the antenna, (picking up the unknown thermal radiation) and a reference temperature (which may be a stable noise source or a temperature sensor within the catheter). This configuration greatly reduces the effects of short-term gain fluctuations in the radiometer. More particularly, the switch provides a mechanism to allow both the reference and the unknown signals to pass through the apparatus essentially at the same time relative to the expected gain drift in the radiometer's amplifiers such that any drifting gain will be applied equally to both the antenna and reference signals.

Since the radiometer input is switched at a constant rate by the Dicke switch between the antenna and the constant-temperature load, the switch-demodulated RF signal should, therefore, be inserted at a point prior to RF amplification in the radiometer and as close to the antenna as possible. Any component or transmission line located between the unknown temperature being detected by the antenna and the Dicke switch can introduce an error. One such error source is the relatively long cable which connects the antenna in the catheter tip to the external radiometer.

In other words, the temperature of that cable contributes to the temperature measurement. The cable temperature is usually not known and varies along the length of the cable. That portion of the cable within the body will be at body temperature, whereas the segment of the cable outside the body will be at room temperature. All of these parameters may vary with the flexing of the cable and the depth of its insertion into the body. Also, when the apparatus includes a transmitter to heat fluid or tissue, some of the transmitter power (about 30 watts) is absorbed by the cable causing the cable to be heated. If the loss in the cable is, say, 3 dB (which could easily be the case), one half of the antenna noise power may come from the desired tissue or fluid volume being examined at the target site and the rest results from the cable. Thus, all errors common to both measurements, i.e., the unknown temperature and the reference temperature, are cancelled in a Dicke-type radiometer. However, any changes or errors between the unknown and the Dicke switch affect only the unknown temperature measurement and are thus not common to both measurement paths.

Accordingly, to achieve accurate temperature measurement, it is highly desirable to minimize the losses between the antenna and the radiometer in order to improve the performance and reliability of the overall apparatus.

2. The Prior Art

One way to minimize such losses and unwanted noise is to minimize the distance between the antenna and the radiometer by locating the radiometer in the catheter, thus essentially eliminating the cable in the receive path as described in U.S. Pat. No. 7,769,469. However, that solution rigidifies the catheter probe and places a lower limit on its diameter making it more difficult to thread the catheter along narrower blood vessels in the body and around sharp turns in such vessels and in other body passages. It also requires that wires extend along the cable to the radiometer.

Thus, there is a need for a microwave heating/sensing catheter apparatus of this general type whose catheter is small and flexible enough to be navigated along such narrower and tortuous paths in the body, yet contributes minimal noise to the overall system.

SUMMARY OF THE INVENTION

Accordingly, it is an object of the present invention to provide an improved microwave heating/sensing catheter apparatus for minimally invasive applications.

Another object of the invention is to provide apparatus of this type whose antenna catheter is quite flexible and has a minimum diameter so that it can be navigated along small blood vessels and other irregular passages in a human or animal body.

A further object of the invention is to provide such apparatus having a reduced sensitivity to unwanted noise so that the apparatus can have an external radiometer.

Yet another object of the invention is to provide apparatus of this type whose antenna catheter has minimal insertion loss.

Other objects will, in part, be obvious and will, in part, appear hereinafter.

The invention accordingly comprises the features of construction, combination of elements and arrangement of parts which will be exemplified in the constructions hereinafter set forth, and the scope of the invention will be indicated in the claims.

In general, my catheter apparatus comprises an antenna catheter for insertion into a natural body passage, e.g., the vasculature, cardio-renal system, gastrointestinal tract, etc. of a human or animal body. When the catheter is to be threaded along narrow blood vessels, the catheter, especially its leading end portion, or probe should have a small diameter and be very flexible. Therefore, a diplexer and radiometer cannot be incorporated into the catheter probe as disclosed in the above patent. Rather, the antenna in the probe is connected to a transmitter and a Dicke-type radiometer located in an external control unit by a special, very low-loss flexible cable to be described later.

On the other hand, when the particular application does not demand such small size and flexibility, the radiometer and/or diplexer may be located anywhere along the cable either inside or outside the body or even in the probe.

When the transmitter is operative, it delivers electromagnetic energy of a first frequency via the cable to the antenna which radiates energy into the adjacent body tissue and/or fluid to heat same. That same antenna also picks up thermal emissions of a higher frequency from that tissue and/or fluid and delivers a corresponding signal via the cable to the radiometer which thereupon outputs a temperature signal indicative of the temperature of the heated tissue and/or fluid. Thus, the apparatus may be used to heat a fluid, e.g. blood, following a selected heating profile, and to heat or ablate tissue to treat tumors, BPH and various renal and cardio-renal diseases by modulating or denervating neurofibers.

To enable the catheter to heat (transmit) and detect temperature (radiometrically sense) simultaneously, a passive diplexer is provided at the proximal end of the cable, the cable and diplexer forming a unique assembly which also allows for cooling of the cable. That is, to minimize component insertion loss, the cable/diplexer assembly provides a reduced cable impedance as well as a fluid path for a coolant delivered from the control unit to the catheter.

Even when the catheter is to be introduced into larger body passages and thus may include an internal diplexer and radiometer as described in the above patent, it is desirable that the catheter apparatus include this special cable to prevent excessive heating of the cable by the transmitter.

As will be described in more detail later, the cable has a hollow center conductor and a relatively low cable impedance, e.g. 30 ohms, compared to the usual 50 ohms. Lowering the cable impedance lowers its insertion loss because, for a given cable outside diameter, the cable's center conductor may be larger, thus increasing its conducting surface area and lowering the current density in that conductor. The hollow center conductor also provides a passage for the aforementioned coolant. The cable's center conductor is surrounded by insulation in the form of one or more filament strands wrapped around the center conductor. These strand (s) improve cable flexibility, while creating spaces that reduce the cable's dielectric constant and thus its insertion loss. These spaces may also provide a return path for a gaseous coolant whose temperature may be controlled to maintain the center conductor at a constant, safe temperature regardless of the level of applied power to the antenna in the catheter thereby to enhance the radiometric sensing capability of the apparatus.

As we shall see, the distal or probe end of the cable may be designed to allow a gaseous coolant to be re-circulated through the catheter or to allow a liquid coolant to be expelled therefrom into a blood vessel or other body passage, e.g. for irrigation. Also, the catheter antenna per se may be attachable to the distal end of the cable to enable the cable to be terminated by different-type antennas. The attachable antenna also allows the cable/diplexer assembly with its lower-impedance cable to be tested by replacing the antenna with a second cable/diplexer assembly and using a standard 50 ohm reflectometer and standard 50 ohm connectors as will be described later.

Thus, the present catheter apparatus with its unique cable/diplexer assembly has a minimum sensitivity to unwanted noise, yet its catheter is able to be navigated along, and around turns in, small blood vessels and other body passages. Therefore, it should find wide application in the non-invasive treatment by heating and ablation of many serious human and animal diseases and abnormalities.

BRIEF DESCRIPTION OF THE DRAWINGS

The invention description below refers to the accompanying drawings, in which.

DETAILED DESCRIPTION OF ILLUSTRATIVE EMBODIMENTS

Figure 1:
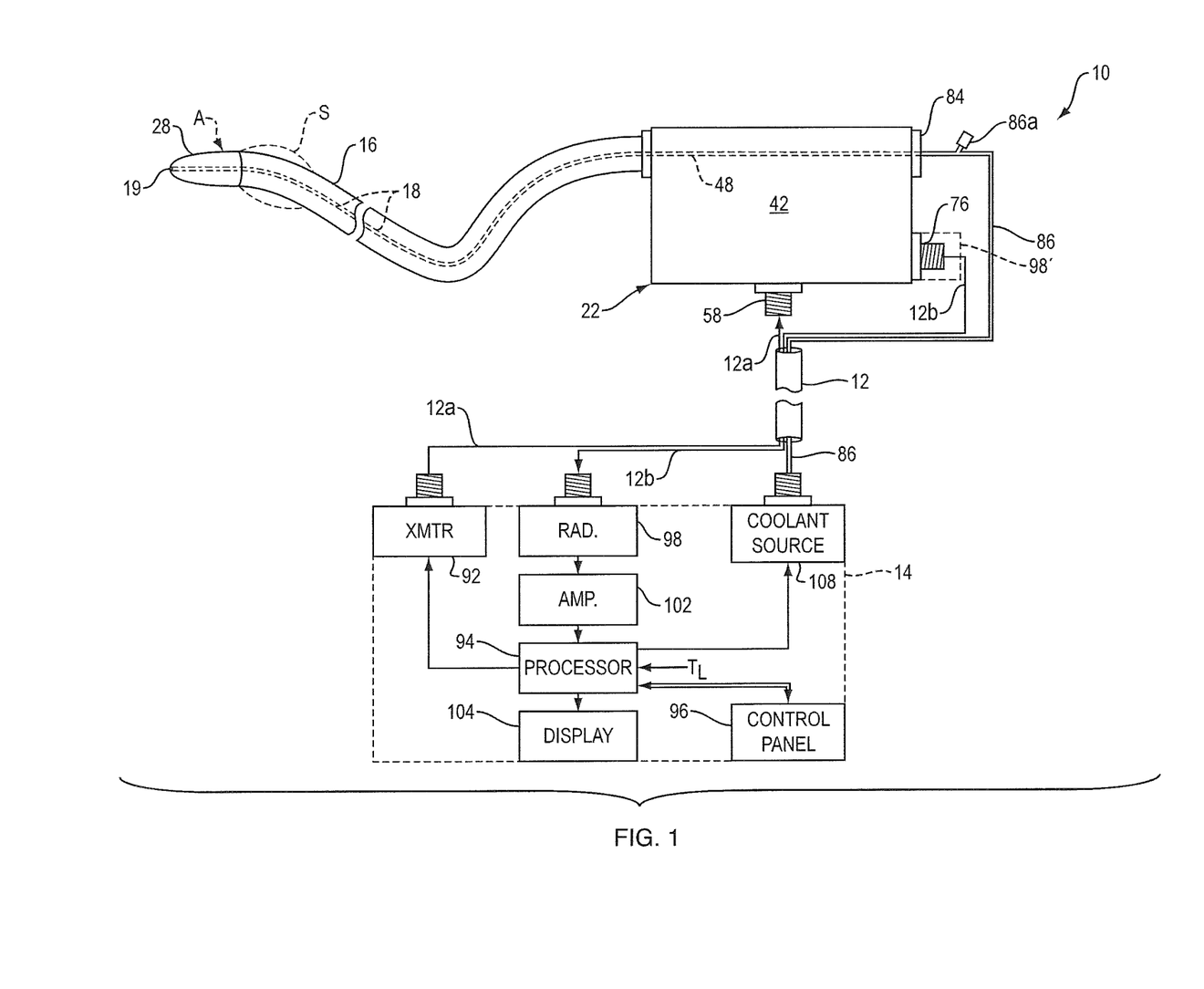
FIG. 1 is a diagrammatic view of heating/sensing catheter apparatus incorporating the invention.

Referring to FIG. 1 of the drawings, the present catheter apparatus comprises an antenna catheter shown generally at 10 connected by a cable 12 to an external control unit 14. Catheter 10 includes a relatively long, e.g. 115 cm, very flexible cable 16 which includes a center conductor 18 extending the entire length of the cable and forming an antenna A at the distal or probe end of the cable. The illustrated antenna A is a monopole, but it may have other forms such as a helix as in U.S. Pat. No. 5,364,336, whose contents hereby is incorporated herein by reference.

In accordance with the invention, center conductor 18 is formed as a thin-wall, e.g. 0.004 inch, tube of soft copper so that it is quite flexible and defines a fluid pathway 19 which extends the entire length of the cable. For example, that center conductor may have an OD of 0.024 inch. The larger diameter, hollow center conductor minimizes the current density thereon for a given cable diameter. This, in turn, minimizes the cable impedance and thus its insertion loss.

The proximal end of cable 16 may connect to a passive diplexer indicated at 22 which allows catheter 10 via antenna A to simultaneously emit electromagnetic energy of a first frequency while picking up thermal radiation of a second frequency. Thus, when cable 16 is navigated along a blood vessel or other body passage or within a catheter guide to position antenna A at a selected target site in a body, catheter 10 may be activated by control unit 14 to heat fluid and/or tissue at the target site to accomplish the desired objective, while at the same time sensing the temperature of the heated fluid and/or tissue thereby enabling control unit 14 to display that temperature and control the heating process. Also as we shall see, the fluid pathway 19 which extends from the catheter through diplexer 22 and along cable 12 to a coolant source in control unit 14 allows a coolant to be flowed along cable 16 to maintain the center conductor 18 thereof at a relatively constant, low temperature. As we shall see, pathway 19 may include a return path from the cable to the coolant source in the event that the coolant is recirculated.

Figure 2A:
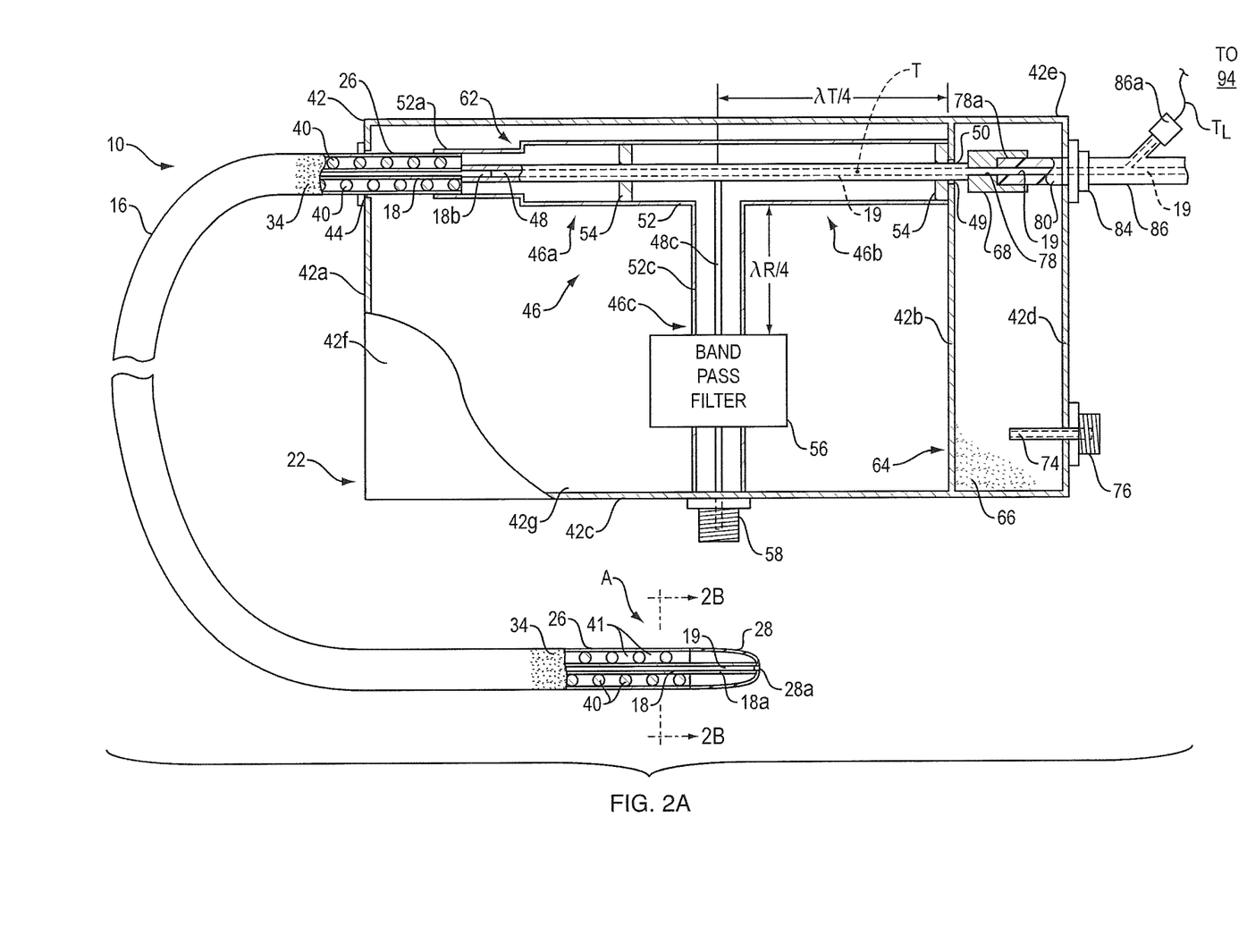
FIG. 2A is a sectional view with parts shown in elevation, on a larger scale, showing the cable/diplexer assembly of the FIG. 1 apparatus in greater detail.
Figure 2B:
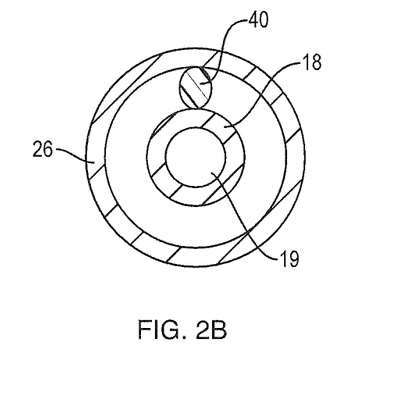
FIG. 2B is a sectional view on a larger scale taken along line 2B-2B of FIG. 2A.

Referring now to FIGS. 2A and 2B, in addition to the hollow center conductor 18, cable 16 has a tubular outer conductor 26 preferably made of metal braid so that it is electrically conductive and quite flexible. The outer conductor 26 may have an ID in the order of 0.042 inch and is shorter than conductor 18 so that a projecting distal end segment 18a of conductor 18 forms antenna A. A hollow cap 28 of a dielectric material is provided at the distal or probe end of the catheter to cover antenna A and provide the probe with a rounded tip. The cap interior, if closed, connects the interior of the center conductor to the annular space between the two conductors. Preferably, the entire length of outer conductor 26 is covered by a layer or jacket 34 of a suitable dielectric material.

As usual with coaxial cables of this general type, the annular space between conductors 18 and 26 may be filled with a dielectric material. In this case, to maximize the flexibility of the cable while dielectrically loading the cable, the insulation is composed of one or more dielectric strands 40, e.g., Teflon® filament, wound around the center conductor 18. A given cable may have many strands 40 or as few as one, depending on the characteristics desired for that cable. In addition to providing flexibility, the filament creates spaces 41 between the filament turns that reduce the dielectric constant of the cable and give it a reduced impedance Z as follows:

$$Z_0 = \frac{138}{\sqrt{\varepsilon}} \log 10 \frac{D}{d} = 30 \text{ ohms}$$

where:
D=outer conductor ID=0.042 in.
d=center conductor OD=0.024 in.
ε=dielectric constant=1.25

As will be described later, the fluid pathway 19 may extend through a hole 28a in the cap 28 as shown in FIG. 2A so that a liquid coolant may be expelled from the catheter or the cap may be closed and a gaseous coolant recirculated back to control unit 14 via a return path constituted by the spaces 41 between the dielectric strand(s) 40.

As shown in FIG. 2A, diplexer 22 includes a housing 42 having an end wall 42a. The proximal end of cable 16 passes through an opening 44 in that wall and connects to one, i.e. the left, arm 46a of a T-stub transmission line shown generally at 46 which may be dielectrically loaded (not shown for clarity). Transmission line 46 includes a hollow center conductor 48 which receives and is connected to a protruding end 18b of cable conductor 18. Thus, conductor 48 continues the fluid pathway 19 from the cable. Transmission line 46 also has a T-shaped outer conductor 52 whose left arm 52a surrounds and connects to cable conductor 26 inside housing 42. The other, i.e. right, arm 46b of transmission line 46 extends to an interior wall 42b of housing 42 and the center conductor 48 thereof passes through a feedthrough 49 in wall 42b. The spacing of the two conductors 48, 52 of the transmission line 46 is maintained by a pair of dielectric spacers 54, 54.

The leg 46c of the T-stub transmission line 46, including a solid center conductor segment 48c and an outer conductor segment 52c, is connected by way of a low pass or band pass filter 56 to a coaxial connector 58 mounted to a side wall 42c of housing 42. The filter 56 may be a conventional printed circuit or a short length of coax (tube filter) which is cut off at the receive frequency. In any event, filter 56 is designed to pass the transmit frequency and block the receive frequency. Thus, transmission line 46 helps to separate the different frequency signals to and from antenna A. More particularly, it forms a quarter wave stub (.lamda..sub.T/4) while also providing a matched 90° bend for a transmitter (heating) signal applied to connector 58 as will be described.

Preferably, a transformer indicated at 62 is provided in the left arm 46a of the transmission line to step up the 30 ohm cable 16 impedance to 50 ohms in the transmission line 46 so that the diplexer 22 can be tested, as will be described, using conventional connectors and test equipment designed for a 50 ohm cable. This impedance transformation may be implemented by stepping the outer conductor arm 52a, e.g. in two steps as shown in FIG. 2A, or by stepping the inner conductor.

Still referring to FIG. 2A, the housing interior wall 42b along with a housing end wall 42d, segments of the housing side walls 42c and 42e, and top wall 42f and bottom wall 42g form a waveguide indicated generally at 64 which may be filled with a dielectric material 66 to minimize its size. The right end of the transmission line center conductor 48 extending through feedthrough 49 is connected to a larger diameter waveguide probe 68 adjacent one narrower wall of waveguide 64, while a waveguide-to-cable transition 74 adjacent the opposite narrower wall projects into the waveguide 64 from a connector 76 mounted to the outside of housing end wall 42d which constitutes a broader wall of the waveguide. As will be seen, that connector may couple the temperature sensing signal from antenna A to a radiometer in control unit 14 (FIG. 1). The waveguide 64 constitutes a high-pass filter that passes the temperature sensing frequency, while blocking the heating frequency. It also provides a DC block, preventing center conductors 18, 48 from coupling directly to a patient. Thus, the combination of this filter and the transmission line 46 enables the diplexer to separate the two signals.

The waveguide probe 68 is unique in that it provides a coolant path as well as a microwave transition. More particularly, probe 68 is formed with an axial passage 78 which is countersunk at 78a to accept an end segment of a tube or conduit 80 of a dielectric material. Tube 80 extends to a connector 84 on housing end wall 42d where it may be connected to a comparable tube 86 extending along cable 12 to control unit 14. Alternatively, of course, tubes 80 and 86 may be a single length of tubing. Thus, probe 68 and tubes 80, 86 provide an extension of the pathway 19 in cable 16. With the inclusion of an injection port 86a in tube 86, the diplexer 22 can provide a path to cable 16 for the injection of a contrast agent to track the position of the catheter via X-ray imaging during a treatment procedure. The injection port 86a will also allow for the insertion of one or more thermocouples T (FIG. 2A) or other type of temperature sensor each having a lead $T_L$ to monitor the temperature of a coolant flowing along fluid pathway 19.

As shown in FIG. 1, the control unit 14 includes a transmitter 92 which delivers power at a microwave heating frequency, e.g. 2.45 GHz to the antenna catheter 10 by way of a cable component 12a connected to connector 58. RF heating may also be employed, e.g. at a frequency of 500 KHz. In either event, transmitter 92 is controlled by a processor 94 which receives instructions via control buttons on a control panel 96 in unit 14. Unit 14 also includes a radiometer 98 which receives the temperature-indicating signal from antenna catheter 10 via a cable component 12b connected to connector 76. The radiometer may have a center frequency of, say, 4 GHz. In order to minimize cable losses between antenna A and the radiometer, the radiometer may be located close to diplexer 22 in an extension of housing 42 as shown in phantom at 98' in FIG. 1 or in cable 12b. In either event, the signal from radiometer 98, 98' is conditioned by an amplifier 102 and routed to processor 94 which may process that signal to control a display 104 which thereupon displays, in real time, the temperature of the fluid and/or tissue being probed by catheter 10. Of course, display 104 can also display other parameters related to the proper operation of the apparatus such as transmitter output power, reflected power, catheter cable temperature, elapsed time, etc.

Unit 14 also includes a coolant source 108 controlled by processor 94 to deliver coolant via tube 86 in cable 12 to antenna catheter 10. For some applications, the coolant may be a liquid, e.g. 0.9% saline, in others, the coolant may be a de-watered gas which has the same microwave characteristics as air, e.g. nitrous oxide. The coolant flows along tube 86 to the fluid pathway 19 in center conductors 18, 48. As the coolant flows along the cable, it maintains the conductors 18 and 48 at a substantially constant relatively low temperature so that they have a relatively low loss regardless of the level of power delivered by transmitter 92. Still, cable 16 has a minimum outside diameter and is quite flexible due to its tubular inner conductor 18, braided outer conductor 26 and intervening spiral dielectric winding strand(s) 40. If the coolant is a liquid, the pathway 19 may extend through a hole 28a in cap 28 as shown in FIG. 2A and irrigate the probed body passage. If the coolant is a gas, the cap may be closed by blocking hole 28a, and the coolant returned to source 108 along a return path provided by a passage from the interior of center conductor 18 to the spaces 41 between strands 40 in cable 16 and pathways (not shown) along diplexer 46 and cable 12 (FIG. 1). If a liquid coolant is to be returned along the cable and not expelled into the probed body passage, that may be done via a conduit extending between outer conductor 26 and jacket 34 or between the jacket and the catheter introducer or guide (not shown) placed in the blood vessel or other body passage prior to insertion of the catheter.

To use the catheter apparatus, a surgeon may insert the probe end of cable 16 into a patient's vasculature or other body passage using a conventional introducer. To facilitate navigating the cable to position its antenna A at a selected target site, a contrast agent may be injected, as needed, into the cable's fluid pathway 19 by way of the injection port 86a or the agent may be added to the coolant supplied by source 108. In either event, the position of the catheter probe may be tracked using a fluoroscope or other X-ray apparatus to position the cable's antenna A at the target site. If desired, the catheter may include a stand off or centering device of a dielectric material shown in phantom at S in FIG. 1 such as the one disclosed in U.S. Pat. No. 6,210,367, the entire contents of which are hereby incorporated herein by reference. This allows the antenna A to ablate tissue in a 360° pattern around the body passage and not just at a single contact point. Once the catheter is in place, the processor 94, following instructions input at control panel 96, may cause coolant source 108 to pump coolant through tube 86 to the pathway 19 in the cable/diplexer assembly 10 to maintain the cable's center conductor 18 and the diplexer's center conductor 48 at a selected relatively low temperature to prevent cable heating due to the power applied by transmitter 92. Since the coolant pathway 19 in the catheter 10 is in the microwave receive path, receiver sensitivity is optimized.

Processor 94 also activates transmitter 92 so that power is delivered via cable component 12a, diplexer 22 and center conductor 18 to antenna A at the probe end of the cable. Antenna A radiates electromagnetic energy at a first frequency, e.g. 2.45 GHz, into the adjacent fluid and/or tissue thereby heating same. At the same time, antenna A picks up thermal emission of a second frequency, e.g. 4 GHz, from that fluid and/or tissue and delivers a corresponding signal via conductor 18, diplexer 22 and cable component 12b to radiometer 98 in control unit 14. That signal is detected by the radiometer and applied to processor 94 to control display 104 which thereupon displays that temperature. Processor 94 may also use that temperature signal to control transmitter 92 to follow a selected heating profile or to maintain the targeted fluid and/or tissue at the desired temperature to achieve a desired result, e.g., warm blood, ablate tissue, denervate neural fibers, etc. All the while, the coolant in fluid pathway 19 maintains the segments of the center conductor 18 of cable 16 both inside and outside the patient at a substantially constant temperature so that the insertion loss of the cable remains low-loss constant throughout the procedure.

As noted above, the temperature sensors T monitor the center conductor 18 temperature at various points along its length. The output(s) of the thermocouple(s) on lead(s) $T_L$ are applied to processor 94 to enable the processor to control coolant source 108 to keep the conductor at a selected temperature, which temperature may be displayed by display 104. Having the injection port 82a located close to waveguide probe 50 allows insertion of thermocouples T, to measure both input and output coolant (conductor 18) temperatures. The coolant also prevents overheating of the cable as a whole to prevent possible injury to the patient.

Figure 3:
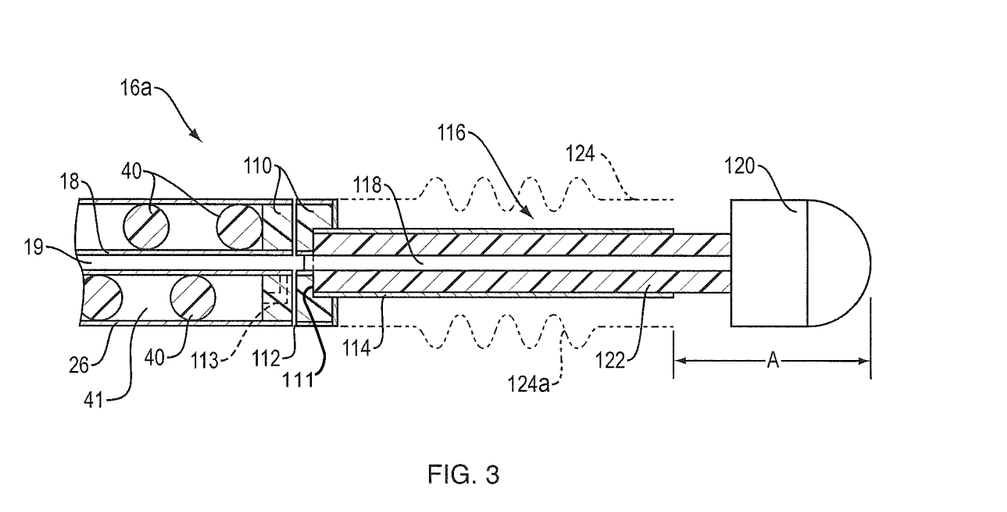
FIG. 3 is a fragmentary sectional view showing a portion of a second cable/diplexer assembly embodiment for use in the FIG. 1 apparatus.

Refer now to FIG. 3 which shows a second cable embodiment 16a for use in the cable/diplexer assembly 10. The components of cable 16a which are in common with cable 16 carry the same identifying numerals. Thus, cable 16a comprises a center conductor 18 defining a fluid pathway 19 and an outer conductor 26 separated by a winding of dielectric strand(s) 40. Cable 16a differs from cable 16 in that its distal end includes a dielectric bead connection device 110 in the form of a bead of a dielectric material. The dielectric bead connection device 110 has a recessed interface 111 at its distal end. If a liquid coolant is to be used, device 110 may be provided with one or more small diameter, e.g. 0.010 inch, radial passages 112 which extend through conductors 18 and 26 to connect the fluid pathway 19 in conductor 18 to the outside. Such holes filled with coolant do not significantly perturb the microwave transmission line comprising cable 16. On the other hand, if the coolant is a gas, it should not enter the blood stream. Therefore, in this event, the passages 112 are not present and a return passage may be provided in device 110 as shown in phantom at 113 in FIG. 3 into the spaces 41 in the cable to return the coolant to coolant source 108.

Center conductor 18 extends to the distal end of bead 110 and the outer conductor 26 wraps around the bead and connects to the outer conductor 114 of a smaller diameter cable extension or probe indicated at 116 when the latter is installed into the recessed interface 111 of the bead 110, as shown in FIG. 3. Extension 116 may be a short length of 30 ohm cable, the center conductor 118 of which may be solid yet quite flexible. More particularly, extension 116 includes a solid wire center conductor 118 whose proximal end plugs into the distal end of hollow center conductor 18. Conductor 118 extends to a conductive end cap 120 spaced beyond the distal end of outer conductor 114 and conductors 114 and 118 are separated by a dielectric material 122 which may consist of wound strand(s) like strand(s) 40. The length of extension 116 beyond outer conductor 114 constitutes the antenna A.

Cable 16a has all of the advantages of cable 16. In addition, its narrower leading end extension 116 is very flexible so that it can be navigated around especially sharp turns in a patient's vasculature and other body passages. Alternatively, extension 116 may have the same diameter as cable 16a but with an outer conductor 124 formed with bellow-like convolutions 124a as shown in phantom in FIG. 3 to maximize its flexibility.

One advantage of this embodiment is that various different type extensions or probes 116 may be plugged into, or otherwise attached to, the end of cable 16a at the recessed interface 111. These extensions may have various diameters and degrees of flexibility. For example, a given extension may have a solid center conductor 118 and a relatively small outside diameter to form a monopole antenna A as shown in solid lines in FIG. 3. Another extension may have a larger diameter as indicated in phantom in FIG. 3 and/or a hollow center conductor to provide a pathway for a liquid coolant in lieu of the passages 112 in connection device 110. Yet another extension may define an antenna A in the form of a helix as in the above U.S. Pat. No. 4,364,336.

Figure 4:
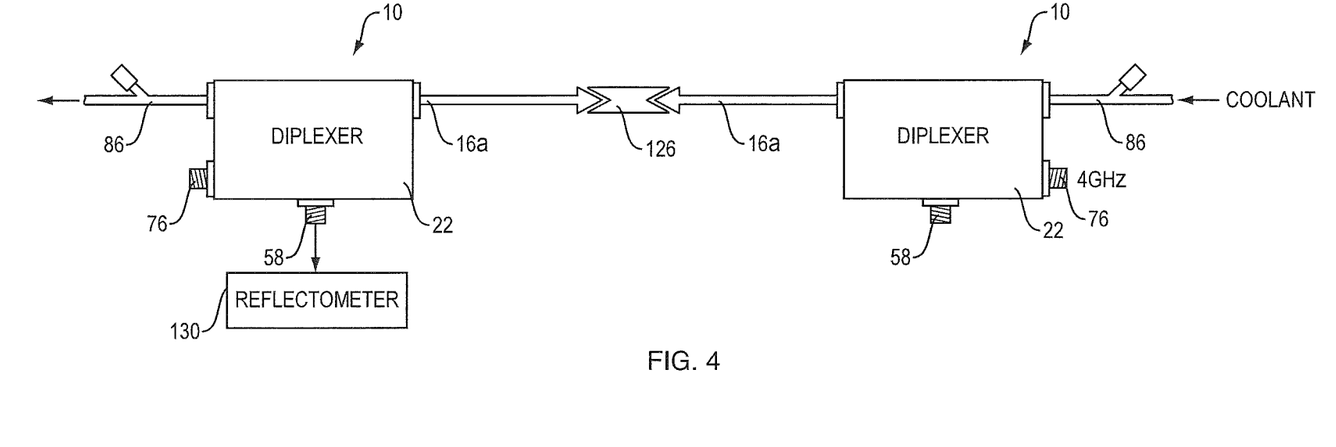
FIG. 4 is a diagrammatic view of an assembly for testing the FIG. 3 cable/diplexer assembly.

In addition, the ability of the extension 116 in FIG. 3 to be formed separately from cable 16a allows the cable/diplexer assembly 10 to be tested using standard 50 ohm connectors and test equipment. More particularly, a pair of the assemblies 10 may be arranged back-to-back as shown in FIG. 4 with the distal ends of their cables 16a, without extensions 116, connected together electrically via a coaxial connector 126. All ports 58, 76 of both diplexers 22 are now at the standard 50 ohm impedance thus allowing the attachment of a standard 50 ohm reflectometer 130 to a connector 58. This enables simultaneous impedance measurements at both the transmitting and receiving frequencies, with or without coolant supplied via tubes 80, 86 and with or without power applied to a connector 76. After such testing, the cable/diplexer assemblies in FIG. 4 may be separated and cable extensions 116 attached to the distal ends of cables 16a prior to use thereof.

Thus, radiometric performance can be obtained with the transmitted power applied and radiometer measurements can be made with or without coolant flowing along pathway 19, and the flow rate and temperature of the coolant can be monitored. Most importantly, all test measurements can be made with commercially available 50 ohm microwave test equipment and connectors.

Figure 5:
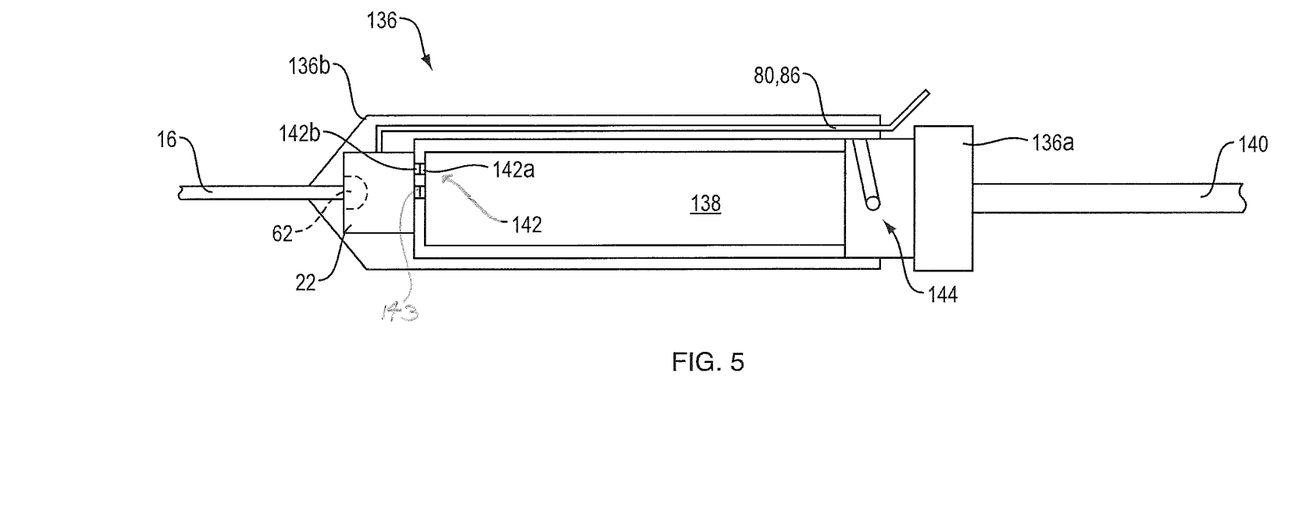
FIG. 5 is a view similar to FIG. 1 of an apparatus embodiment with a disposable catheter cable and handle.

Providing catheter apparatus whose radiometer is external to the patient allows the option of making the cables 16, 16a and diplexer 46 as a disposable item. FIG. 5 illustrates an antenna catheter indicated at 136 composed of two separate but connectable parts 136a and 136b. Part 136a is a barrel-like re-usable part which may contain a radiometer 138 and an external cable 140, comparable to cable 12, for connection to transmitter 92, amplifier 102 and coolant source 108 in control unit 14. Part 136a also has end contacts 142a which engage mating contacts 142b of part 136b when the two parts interfit as shown in FIG. 5. The mating contacts 142a, 142b may be part of a more or less conventional 50 ohm blind mate coaxial connector 142. Also, there is a coolant line connection 143 between parts 136a and 136b.

Part 136b is a sleeve-like disposable part which may encircle part 136a and be releasably locked thereto by any conventional locking means 144, such as mating threads, bayonet connection, spring-loaded pin, etc. Part 136b may include the catheter cable 16 or 16a, transformer 62 and diplexer 22 along with a segment of coolant tube 80 and perhaps tube 86. When assembled as shown, parts 136a, 136b may function as a catheter handle for cable 16 during a procedure. When the procedure is completed, these parts may be separated and part 136b, including its cable 16, may be disposed of in proper fashion.

Other partly disposable antenna catheters may be envisioned. For example, the disposable part may include only the catheter cable 16 and the transformer 62, the re-usable part having the diplexer 46, radiometer 98 and the cable 140.

Also as mentioned above, the radiometer and/or diplexer may be incorporated into the cable at any point along its length either inside or outside the body; see U.S. Pat. Nos. 7,197,356 and 7,769,469, the contents of which are hereby incorporated herein by reference. Also, the radiometer need not be integrated with the diplexer as in FIG. 5. Of course, there is no size (diameter) constraint on any segment of the cable outside the body.

Figure 6:
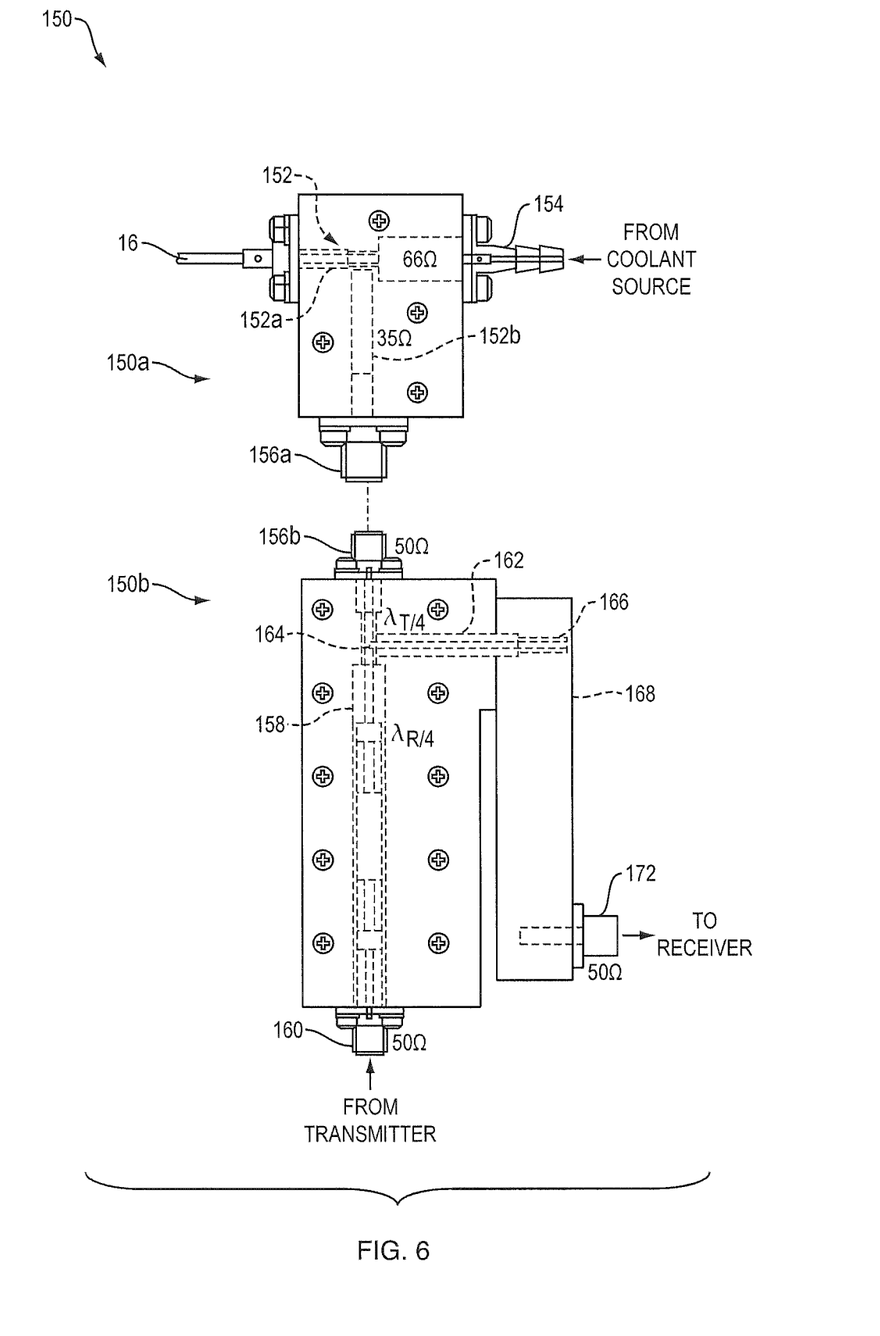
FIG. 6 is a similar view of still another apparatus embodiment.

Refer now to FIG. 6 which illustrates another antenna catheter apparatus embodiment shown generally at 150 composed of a disposable part 150a and a re-usable part 150b. The proximal end of cable 16 is connected to part 150a which includes a T-shaped transmission line 152 whose arms 152a have a tubular inner conductor leading to a coolant connecter 154 mounted to the side of unit 150a. Connector 154 may be coupled to a tube similar to tube 86 leading to a coolant source and having a port for the introduction of a contrast agent, thermocouple, etc. as described above. As before, the transmission line serves both as a coolant path and a transformer, i.e. 30/50 ohms. Transmission line 152 includes a branch or leg 152b leading to a standard 50 ohm port 156a mounted to the bottom of part 150a. Port 156a is adapted to be connected to a mating 50 ohm port 156b mounted to the top of part 150b. Part 150b contains a transmission line 158 which connects port 156b to a similar port 160 mounted to the bottom of part 150b. Also, a coaxial branch 162 extends from a dipole junction 164 in transmission line 158 to a waveguide-to-coaxial probe 156 adjacent to one end of a waveguide 168. A waveguide-to-coaxial port 172 is present adjacent the opposite end of the waveguide.

The apparatus embodiment 150 operates in more or less the same way as apparatus 10. When port 160 is connected to a transmitter and port 172 is connected to a radiometer, the transmission line 158 functions as a low pass or band pass filter in the antenna transmit path and the waveguide 168 functions as a high pass, low loss filter in the receive path thereby separating the signals to and from the antenna at the distal end of cable 16, while at the same time matching the impedance of cable 16 to the impedance of the standard 50 ohm ports 160, 172. Apparatus 150 has an advantage over apparatus 136 shown in FIG. 5 in that the coolant is not routed through part 150b containing the diplexer per se. Thus, there is no need for a fluid connection like connection 143 between the disposable part 150a and the reusable part 150b. Yet, the coolant is still routed along most of the receive signal path from the antenna so as to obtain the advantages discussed above.

It should be understood that while we have shown the high pass filter component of the diplexers in apparatus 10 and 150 as being a waveguide, it may just as well be a more or less conventional printed transmission line structure e.g. stripline, suspended substrate, microstrip, etc. For example, a high pass filter of the suspended substrate type may include a metal enclosure having a rectangular cross-section and containing a printed circuit board spanning the narrow walls of the enclosure, the board bearing metalized strips on opposite faces of the board which are centered in the enclosure. The circuit board may be formed with a coolant path extending along the board between the metal strips where there is no microwave field so that the coolant does not adversely affect the operation of the diplexer. Of course, if that type of filter should be used in the FIG. 6 apparatus embodiment, no such cooling passage would be required.

It will thus be seen that the objects set forth above, among those made apparent from the preceding description, are efficiently attained. Also, certain changes may be made in the above constructions without departing from the scope of the invention. For example, in a given application, instead of ablating tissue using electromagnetic energy as described above, a cryogenic fluid, e.g. nitrous oxide, from coolant source 108 may be circulated through the catheter to cause tissue ablation or renal denervation by freezing the tissue; the temperature measurement process using the antenna catheter remains the same. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. An internally cooled catheter apparatus comprising:
an elongated flexible coaxial cable having proximal and distal ends, said cable including a hollow center conductor, an outer conductor and an electrically insulating layer in an annular space between said conductors substantially along the length of the cable;
an antenna at the distal end of the cable; and
a diplexer including a branched transmission line comprised of a common path with a tubular inner conductor segment one end of which is connected to the center conductor of the cable at the proximal end of the cable, a transmit path configured for connecting the common path to a transmitter which transmits signals of a first frequency range, and a receive path configured for connecting the common path to a receiver which detects signals of a second frequency range, the receive path having the tubular inner conductor segment of the common path extending therethrough and adapted for connection to a coolant source, the center conductor and the tubular inner conductor forming a continuous coolant pathway,
wherein said diplexer is for isolating the signals on the transmit path from the signals on the receive path.

2. The apparatus defined in claim 1 wherein said receive path includes a first electrical filter.

3. The apparatus defined in claim 2, wherein:
said first electrical filter comprises a waveguide with opposite ends, said inner conductor segment extending into the waveguide adjacent one end thereof and forming a tubular probe therein;
said apparatus further comprises a dielectric conduit connected to the tubular probe, extending out of the waveguide, and adapted for connection to a coolant source, thereby continuing the coolant pathway; and
said first electrical filter further comprises a waveguide-to-cable transition adjacent the other end of the waveguide and adapted for connection to the receiver.

4. The apparatus defined in claim 3 wherein the waveguide is loaded with a dielectric material.

5. The apparatus defined in claim 3 wherein:
the diplexer comprises a housing containing the branched transmission line and the waveguide; and
said dielectric conduit extends from the probe to the housing exterior and includes an injection port outside the housing.

6. The apparatus defined in claim 1 wherein the branched transmission line is a T-shaped transmission line, said transmit path including a second electrical filter.

7. The apparatus defined in claim 1, wherein:
said receive path comprises a waveguide with opposite ends, said tubular inner conductor segment extending into the waveguide adjacent one end thereof forming a probe therein, and
said waveguide comprises a waveguide-to-cable transition adjacent the other end of the waveguide and adapted for connection to a receiver.

8. The apparatus defined in claim 1, further comprising an impedance-matching transformer in series with the cable and the common path.

9. The apparatus defined in claim 1 wherein the cable outer conductor comprises braided conductive strands.

10. The apparatus defined in claim 1 wherein the cable insulating layer comprises a flexible winding of one or more dielectric strands defining multiple annular flow paths therebetween.

11. The apparatus defined in claim 1 wherein said antenna comprises an extension of the center conductor beyond the outer conductor and the insulating layer at the distal end of the cable.

12. The apparatus defined in claim 11 wherein said antenna further comprises a hollow cap enclosing the center conductor extension, the center conductor extension continuing said coolant pathway to an opening at the distal end of the cap.

13. The apparatus defined in claim 1 wherein the distal end of the cable comprises a bead of dielectric material having a recessed interface.

14. The apparatus defined in claim 13 wherein the bead of dielectric material defines radial passages for extending the coolant pathway from the interior of the center conductor to an exterior surface of the cable outer conductor.

15. The apparatus defined in claim 13 wherein the cable insulating layer comprises a non-rigid winding of one or more dielectric strands defining multiple fluid flow paths therebetween, wherein the bead of dielectric material defines a coolant path between the interior of the center conductor and said annular space so that said annular space can provide a coolant return path along the cable.

16. The apparatus defined in claim 13, further comprising a cable extension including a central extension conductor, an outer extension conductor surrounding at least a proximal portion of the central extension conductor, and a dielectric layer disposed between the central extension conductor and the outer extension conductor, wherein the dielectric bead recessed interface is configured to mechanically and electrically connect a proximal end of the cable extension to the coaxial cable at the distal end thereof.

17. The apparatus defined in claim 16, wherein the central extension conductor is hollow and extends the continuous coolant pathway to a distal end of the cable extension.

18. The apparatus defined in claim 16, wherein:
the dielectric bead further comprises a portion of the cable outer conductor on a distal face thereof about the recessed interface and configured to be in electrical communication with the outer extension conductor when a proximal end of the cable extension is disposed within the recessed interface; and
the cable center conductor terminates at the dielectric bead recessed interface and configured to be in electrical communication with the central extension conductor when the proximal end of the cable extension is disposed within the recessed interface.

19. The apparatus defined in claim 16, further comprising an insulating bellows surrounding the cable extension.

20. The apparatus defined in claim 16, further comprising an antenna disposed at a distal end of the cable extension.

21. The apparatus defined in claim 20 wherein the antenna comprises the central extension conductor extending beyond the outer extension conductor and the dielectric layer disposed between the central extension conductor and the outer extension conductor at the distal end of the cable.

22. The apparatus defined in claim 21 and further including a peripheral dielectric stand-off adjacent to and surrounding the distal end of the cable extension for distancing the antenna from a wall in a body passage.

23. The apparatus defined in claim 1, wherein the coolant pathway is selected from the group consisting of a gaseous coolant pathway and a liquid coolant pathway.

24. The apparatus of claim 1 wherein the antenna is flexible.

25. The apparatus defined in claim 1 and further including a peripheral dielectric stand-off adjacent to and surrounding the distal end of the cable for distancing said antenna from a wall within in a body passage.

26. The apparatus defined in claim 1 and further including one or more temperature detectors positioned in said coolant pathway for monitoring the temperature of the coaxial cable at one or more locations therealong.

27. The apparatus defined in claim 1 and further including an injection port for introducing an x-ray contrast agent into said coolant pathway.

28. The apparatus defined in claim 1 wherein the transmitter is a microwave or RF transmitter.

29. The apparatus defined in claim 1 and further including the coolant source connected to said tubular inner conductor segment.

30. An internally cooled catheter apparatus comprising:
an elongated flexible coaxial cable having proximal and distal ends, said cable including:
a hollow, tubular center electrical conductor defining a coolant pathway extending the length of the cable;
a tubular outer electrical conductor disposed about the center conductor; and
an electrical insulating layer in an annular space between said center and outer conductors along the length of the center and outer conductors between the proximal and distal ends, said insulating layer being constituted by one or more windings of a dielectric material;
a dielectric bead connection device having a proximal end at the distal end of the cable and an opposite distal end, the center electrical conductor extending through the dielectric bead connection device to the distal end thereof, the dielectric bead connection device comprising an interface at the distal end of the dielectric bead connection device for connecting a cable extension thereto; and
a diplexer including a branched transmission line comprised of a common path with a tubular inner conductor segment one end of which is connected to the center conductor of the cable at the proximal end of the cable, a transmit path configured for connecting the common path to a transmitter which transmits signals of a first frequency range, and a receive path configured for connecting the common path to a receiver which detects signals of a second frequency range, the receive path having the tubular inner conductor segment of the common path extending therethrough and adapted for connection to a coolant source, the tubular inner conductor being in communication with the coolant pathway defined by the hollow, tubular center conductor and forming an extension of the coolant pathway, the center conductor and the tubular inner conductor forming a continuous coolant pathway, and
wherein said diplexer is for isolating the signals on the transmit path from the signals on the receive path.

31. The apparatus of claim 13, further comprising the coolant source; wherein the coolant source is a source of gaseous coolant,
wherein the one or more windings of dielectric material define multiple coolant flow paths therebetween along the annular space, and
wherein the dielectric bead connection device defines at least one return path between the interior of the center conductor and the multiple coolant flow paths so that the annular space provides a gaseous coolant return path along the cable.

32. The apparatus defined in claim 31, whereby the gaseous coolant is conveyed along the length of the center conductor to the distal end of the cable and into the dielectric bead connection device, enters the multiple coolant flow paths defined by the one or more windings of dielectric material via the at least one return path between the coolant pathway and the multiple coolant flow paths, and exhausts from the proximal end of the multiple coolant flow paths thereby cooling the center conductor.

33. The apparatus defined in claim 30, wherein the interface is a recessed interface at the distal end of the dielectric bead connection device, the outer conductor extending at least onto a distal surface of the dielectric bead connection device and the center conductor extending through the dielectric bead connection device to a point proximate said recessed interface.

34. The apparatus defined in claim 33, further comprising the cable extension connected to the interface, the cable extension having an antenna center conductor, a proximal end of the cable extension configured to be mechanically retained within the recessed interface of the dielectric bead connection device, whereby the antenna center conductor is in electrical communication with the cable center conductor extending through the dielectric bead connection device to the point proximate the recessed interface.

35. The apparatus of claim 34, wherein the antenna center conductor of the cable extension is tubular and continues the coolant pathway of the hollow, tubular center electrical conductor to a distal end of the cable extension when the cable extension is connected to the interface of the dielectric bead connection device.

36. The apparatus defined in claim 30 and further including an impedance-matching transformer in series between the cable and the common path.

37. The apparatus defined in claim 30 wherein said branched transmission line is comprised of a T-shaped transmission line.

38. The apparatus defined in claim 30, further comprising a first housing, a second housing, and the receiver,
  wherein said cable extends from the first housing,
  wherein said receiver is disposed within the second housing,
  wherein said first and second housings are configured for mutual reversible mechanical engagement, and
  wherein said first and second housings are configured to electrically extend the cable to the receiver in the second housing.

39. The apparatus defined in claim 30 wherein said outer conductor comprises braided conductive strands.

40. The apparatus defined in claim 30 and further including one or more temperature sensors in said center conductor.

41. The apparatus of claim 13, further comprising the cable extension disposed at the distal end of the dielectric bead connection device.

42. The apparatus of claim 13, further comprising the coolant source; wherein the coolant source is a source of cryogenic fluid, and
  wherein the dielectric bead connection device defines radial passages for extending the coolant pathway from the interior of the center conductor to an exterior surface of the cable outer conductor.

* * * * *